(12) United States Patent
Stern et al.

(10) Patent No.: US 7,344,535 B2
(45) Date of Patent: Mar. 18, 2008

(54) DEVICES AND METHODS FOR TREATMENT OF LUMINAL TISSUE

(75) Inventors: Roger A. Stern, Cupertino, CA (US); Jerome Jackson, Los Altos, CA (US); Vincent N. Sullivan, San Jose, CA (US); George H. Smith, Palo Alto, CA (US); Roy D. Corbitt, Santa Clara, CA (US); Jennifer A. Hodor, Sunnyvale, CA (US); Carson J. Shellengberger, Larkspur, CO (US)

(73) Assignee: Barrx Medical, Inc., Sunnyvale, CA (US)

( * ) Notice: Subject to any disclaimer, the term of this patent is extended or adjusted under 35 U.S.C. 154(b) by 0 days.

(21) Appl. No.: 11/557,445

(22) Filed: Nov. 7, 2006

(65) Prior Publication Data

US 2007/0066973 A1 Mar. 22, 2007

Related U.S. Application Data

(62) Division of application No. 10/754,444, filed on Jan. 9, 2004, now Pat. No. 7,150,745.

(51) Int. Cl.
*A61B 18/14* (2006.01)
(52) U.S. Cl. .......................... 606/41; 606/49; 606/50; 607/133
(58) Field of Classification Search .................. 606/41, 606/48–50; 607/133
See application file for complete search history.

(56) References Cited

U.S. PATENT DOCUMENTS

| | | |
|---|---|---|
| 1,798,902 A | 3/1931 | Raney |
| 3,517,128 A | 6/1970 | Hines |
| 3,901,241 A | 8/1975 | Allen, Jr. |
| 4,011,872 A | 3/1977 | Komiya |
| 4,196,724 A | 4/1980 | Wirt et al. |
| 4,304,239 A | 12/1981 | Perlin |
| 4,411,266 A | 10/1983 | Cosman |

(Continued)

FOREIGN PATENT DOCUMENTS

DE 3838840 5/1990

(Continued)

OTHER PUBLICATIONS

Castell, D.O. Gastroesophageal Reflux Disease: Current Strategies for Patient Management Arch Fam Med. 1996; 5(4):221-227.

(Continued)

*Primary Examiner*—Michael Peffley
*Assistant Examiner*—Alex Toy
(74) *Attorney, Agent, or Firm*—Shay Glenn LLP

(57) ABSTRACT

Devices and methods are provided for treatment of tissue in a body lumen with an electrode deployment device. Embodiments typically include a device with a plurality of electrodes having a pre-selected electrode density arranged on the surface of a support. The support may comprise a non-distensible electrode backing that is spirally furled about an axis and coupled to an expansion member such as an inflatable elastic balloon. In some embodiments, the balloon is inflated to selectively expose a portion of the electrode surface while maintaining the electrode density.

13 Claims, 9 Drawing Sheets

U.S. PATENT DOCUMENTS

| | | | |
|---|---|---|---|
| 4,423,812 A | 1/1984 | Sato | |
| 4,532,924 A | 8/1985 | Auth et al. | |
| 4,565,200 A | 1/1986 | Cosman | |
| 4,640,298 A | 2/1987 | Pless et al. | |
| 4,658,836 A | 4/1987 | Turner | |
| 4,674,481 A | 6/1987 | Boddie, Jr. et al. | |
| 4,676,258 A | 6/1987 | Inokuchi et al. | |
| 4,705,041 A | 11/1987 | Kim | |
| 4,740,207 A * | 4/1988 | Kreamer | 623/1.15 |
| 4,765,331 A | 8/1988 | Petruzzi et al. | |
| 4,776,349 A | 10/1988 | Nashef et al. | |
| 4,887,614 A | 12/1989 | Shirakami et al. | |
| 4,901,737 A | 2/1990 | Toone | |
| 4,906,203 A | 3/1990 | Margrave et al. | |
| 4,907,589 A | 3/1990 | Cosman | |
| 4,930,521 A | 6/1990 | Metzger et al. | |
| 4,943,290 A | 7/1990 | Rexroth et al. | |
| 4,947,842 A | 8/1990 | Marchosky et al. | |
| 4,949,147 A | 8/1990 | Bacuvier | |
| 4,955,377 A | 9/1990 | Lennox et al. | |
| 4,966,597 A | 10/1990 | Cosman | |
| 4,969,890 A * | 11/1990 | Sugita et al. | 606/192 |
| 4,976,711 A | 12/1990 | Parins et al. | |
| 4,979,948 A | 12/1990 | Geddes et al. | |
| 4,998,539 A * | 3/1991 | Delsanti | 128/898 |
| 5,006,119 A | 4/1991 | Acker et al. | |
| 5,010,895 A * | 4/1991 | Maurer et al. | 607/138 |
| 5,019,075 A | 5/1991 | Spears et al. | |
| 5,045,056 A | 9/1991 | Behl | |
| 5,046,512 A | 9/1991 | Murchie | |
| 5,047,028 A | 9/1991 | Qian | |
| 5,056,532 A | 10/1991 | Hull et al. | |
| 5,057,107 A | 10/1991 | Parins et al. | |
| 5,078,717 A | 1/1992 | Parins et al. | |
| 5,083,565 A | 1/1992 | Parins | |
| 5,084,044 A | 1/1992 | Quint | |
| 5,088,979 A | 2/1992 | Filipi et al. | |
| 5,094,233 A | 3/1992 | Brennan | |
| 5,100,423 A | 3/1992 | Fearnot | |
| 5,106,360 A | 4/1992 | Ishiwara et al. | |
| 5,117,828 A | 6/1992 | Metzger et al. | |
| 5,122,137 A | 6/1992 | Lennox | |
| 5,125,928 A | 6/1992 | Parins et al. | |
| 5,151,100 A | 9/1992 | Abele et al. | |
| 5,156,151 A | 10/1992 | Imran | |
| 5,190,541 A | 3/1993 | Abele et al. | |
| 5,192,297 A * | 3/1993 | Hull | 623/1.11 |
| 5,197,963 A | 3/1993 | Parins | |
| 5,197,964 A | 3/1993 | Parins | |
| 5,205,287 A | 4/1993 | Erbel et al. | |
| 5,215,103 A | 6/1993 | Desai | |
| 5,232,444 A | 8/1993 | Just et al. | |
| 5,236,413 A | 8/1993 | Feiring | |
| 5,242,441 A | 9/1993 | Avitall | |
| 5,254,126 A | 10/1993 | Filipi et al. | |
| 5,256,138 A | 10/1993 | Burek et al. | |
| 5,257,451 A | 11/1993 | Edwards et al. | |
| 5,263,493 A | 11/1993 | Avitall | |
| 5,275,162 A | 1/1994 | Edwards et al. | |
| 5,275,169 A | 1/1994 | Afromowitz et al. | |
| 5,275,608 A | 1/1994 | Forman et al. | |
| 5,275,610 A | 1/1994 | Eberbach | |
| 5,277,201 A | 1/1994 | Stern | |
| 5,281,216 A | 1/1994 | Klicek | |
| 5,281,217 A | 1/1994 | Edwards et al. | |
| 5,281,218 A | 1/1994 | Imran | |
| 5,290,286 A | 3/1994 | Parins | |
| 5,292,321 A | 3/1994 | Lee | |
| 5,293,869 A | 3/1994 | Edwards et al. | |
| 5,305,696 A | 4/1994 | Mendenhall | |
| 5,309,910 A | 5/1994 | Edwards et al. | |
| 5,313,943 A | 5/1994 | Houser et al. | |
| 5,314,466 A | 5/1994 | Stern et al. | |
| 5,316,020 A | 5/1994 | Truffer | |
| 5,324,284 A | 6/1994 | Imran | |
| 5,328,467 A | 7/1994 | Edwards et al. | |
| 5,334,196 A | 8/1994 | Scott et al. | |
| 5,336,222 A | 8/1994 | Durgin, Jr. et al. | |
| 5,345,936 A | 9/1994 | Pomeranz et al. | |
| 5,348,554 A | 9/1994 | Imran et al. | |
| 5,363,861 A | 11/1994 | Edwards et al. | |
| 5,365,926 A | 11/1994 | Desai | |
| 5,365,945 A | 11/1994 | Halstrom | |
| 5,366,490 A | 11/1994 | Edwards et al. | |
| 5,368,557 A | 11/1994 | Nita et al. | |
| 5,368,592 A | 11/1994 | Stern et al. | |
| 5,370,675 A | 12/1994 | Edwards et al. | |
| 5,370,678 A | 12/1994 | Edwards et al. | |
| 5,383,876 A | 1/1995 | Nardella | |
| 5,383,917 A | 1/1995 | Desai et al. | |
| 5,385,544 A | 1/1995 | Edwards et al. | |
| 5,397,339 A | 3/1995 | Desai | |
| 5,398,683 A | 3/1995 | Edwards et al. | |
| 5,401,272 A | 3/1995 | Perkins | |
| 5,403,311 A | 4/1995 | Abele et al. | |
| 5,409,453 A | 4/1995 | Lundquist et al. | |
| 5,409,483 A | 4/1995 | Campbell et al. | |
| 5,415,657 A | 5/1995 | Taymor-Luria | |
| 5,421,819 A | 6/1995 | Edwards et al. | |
| 5,423,808 A | 6/1995 | Edwards et al. | |
| 5,423,811 A | 6/1995 | Imran et al. | |
| 5,423,812 A | 6/1995 | Ellman et al. | |
| 5,428,658 A | 6/1995 | Oettinger et al. | |
| 5,433,739 A | 7/1995 | Sluijter et al. | |
| 5,435,805 A | 7/1995 | Edwards | |
| 5,441,499 A | 8/1995 | Fritzsch | |
| 5,443,470 A | 8/1995 | Stern et al. | |
| 5,454,782 A | 10/1995 | Perkins | |
| 5,454,809 A | 10/1995 | Janssen | |
| 5,456,662 A | 10/1995 | Edwards et al. | |
| 5,456,682 A | 10/1995 | Edwards et al. | |
| 5,458,596 A | 10/1995 | Lax et al. | |
| 5,458,597 A | 10/1995 | Edwards et al. | |
| 5,462,545 A * | 10/1995 | Wang et al. | 606/41 |
| 5,465,717 A | 11/1995 | Imran et al. | |
| 5,470,308 A | 11/1995 | Edwards et al. | |
| 5,471,982 A | 12/1995 | Edwards et al. | |
| 5,472,441 A | 12/1995 | Edwards et al. | |
| 5,484,400 A | 1/1996 | Edwards et al. | |
| 5,486,161 A | 1/1996 | Lax et al. | |
| 5,490,984 A | 2/1996 | Freed | |
| 5,496,271 A | 3/1996 | Burton et al. | |
| 5,496,311 A | 3/1996 | Abele et al. | |
| 5,500,012 A | 3/1996 | Brucker et al. | |
| 5,505,728 A | 4/1996 | Ellman et al. | |
| 5,505,730 A | 4/1996 | Edwards | |
| 5,507,743 A | 4/1996 | Edwards et al. | |
| 5,509,419 A | 4/1996 | Edwards et al. | |
| 5,514,130 A | 5/1996 | Baker | |
| 5,514,131 A | 5/1996 | Edwards et al. | |
| 5,517,989 A * | 5/1996 | Frisbie et al. | 600/585 |
| 5,520,684 A | 5/1996 | Imran | |
| 5,522,815 A | 6/1996 | Durgin, Jr. et al. | |
| 5,531,676 A | 7/1996 | Edwards et al. | |
| 5,531,677 A | 7/1996 | Lundquist et al. | |
| 5,533,958 A * | 7/1996 | Wilk | 600/18 |
| 5,536,240 A | 7/1996 | Edwards et al. | |
| 5,536,267 A | 7/1996 | Edwards et al. | |
| 5,540,655 A | 7/1996 | Edwards et al. | |
| 5,542,916 A | 8/1996 | Hirsch et al. | |
| 5,542,928 A | 8/1996 | Evans et al. | |
| 5,549,644 A | 8/1996 | Lundquist et al. | |
| 5,549,661 A | 8/1996 | Kordis et al. | |
| 5,554,110 A | 9/1996 | Edwards et al. | |

| | | | | | | |
|---|---|---|---|---|---|---|
| 5,556,377 | A | 9/1996 | Rosen et al. | 6,179,836 B1 | 1/2001 | Eggers et al. |
| 5,558,672 | A | 9/1996 | Edwards et al. | 6,182,666 B1 | 2/2001 | Dobak, III |
| 5,558,673 | A | 9/1996 | Edwards et al. | 6,197,022 B1 | 3/2001 | Baker |
| 5,562,720 | A | 10/1996 | Stern et al. | 6,237,355 B1 | 5/2001 | Li |
| 5,566,221 | A | 10/1996 | Smith et al. | 6,238,392 B1 | 5/2001 | Long |
| 5,569,241 | A | 10/1996 | Edwards | 6,254,598 B1 * | 7/2001 | Edwards et al. ............. 606/41 |
| 5,571,116 | A | 11/1996 | Bolanos et al. | 6,258,087 B1 | 7/2001 | Edwards et al. |
| 5,578,007 | A | 11/1996 | Imran | 6,258,118 B1 * | 7/2001 | Baum et al. ............... 623/1.19 |
| 5,588,432 | A | 12/1996 | Crowley | 6,273,886 B1 | 8/2001 | Edwards et al. |
| 5,588,960 | A | 12/1996 | Edwards et al. | 6,321,121 B1 | 11/2001 | Zelickson et al. |
| 5,591,195 | A | 1/1997 | Taheri et al. | 6,325,798 B1 | 12/2001 | Edwards et al. |
| 5,599,345 | A | 2/1997 | Edwards et al. | 6,325,800 B1 | 12/2001 | Durgin et al. |
| 5,609,151 | A | 3/1997 | Mulier et al. | 6,355,031 B1 | 3/2002 | Edwards et al. |
| 5,621,780 | A | 4/1997 | Smith et al. | 6,355,032 B1 | 3/2002 | Hovda et al. |
| 5,624,439 | A | 4/1997 | Edwards et al. | 6,358,245 B1 | 3/2002 | Edwards et al. |
| 5,651,780 | A | 7/1997 | Jackson et al. | 6,363,937 B1 | 4/2002 | Hovda et al. |
| 5,658,278 | A | 8/1997 | Imran et al. | 6,383,181 B1 | 5/2002 | Johnston et al. |
| 5,672,153 | A | 9/1997 | Lax et al. | 6,394,949 B1 | 5/2002 | Crowley et al. |
| 5,676,674 | A | 10/1997 | Bolanos et al. | 6,402,744 B2 | 6/2002 | Edwards et al. |
| 5,688,266 | A | 11/1997 | Edwards et al. | 6,405,732 B1 | 6/2002 | Edwards et al. |
| 5,688,490 | A | 11/1997 | Tournier et al. | 6,409,723 B1 | 6/2002 | Edwards |
| 5,702,438 | A | 12/1997 | Avitall | 6,415,016 B1 | 7/2002 | Chornenky et al. |
| 5,709,224 | A | 1/1998 | Behl et al. | 6,423,058 B1 | 7/2002 | Edwards et al. |
| 5,713,942 | A | 2/1998 | Stern et al. | 6,425,877 B1 | 7/2002 | Edwards |
| 5,716,410 | A * | 2/1998 | Wang et al. ................. 606/191 | 6,428,536 B2 | 8/2002 | Panescu et al. |
| 5,730,128 | A | 3/1998 | Pomeranz et al. | 6,432,104 B1 | 8/2002 | Durgin et al. |
| 5,732,698 | A | 3/1998 | Swanson et al. | 6,440,128 B1 | 8/2002 | Edwards et al. |
| 5,738,096 | A | 4/1998 | Ben-Haim | 6,448,658 B2 | 9/2002 | Takata et al. |
| 5,748,699 | A | 5/1998 | Smith | 6,454,790 B1 | 9/2002 | Neuberger et al. |
| 5,769,846 | A | 6/1998 | Edwards et al. | 6,464,697 B1 | 10/2002 | Edwards et al. |
| 5,769,880 | A | 6/1998 | Truckai et al. | 6,544,226 B1 | 4/2003 | Gaiser et al. |
| 5,800,334 | A * | 9/1998 | Wilk ........................... 600/18 | 6,547,776 B1 | 4/2003 | Gaiser et al. |
| 5,800,429 | A | 9/1998 | Edwards | 6,547,787 B1 | 4/2003 | Altman et al. |
| 5,820,629 | A * | 10/1998 | Cox ........................... 606/159 | 6,551,302 B1 | 4/2003 | Rosinko et al. |
| 5,823,197 | A | 10/1998 | Edwards | 6,551,310 B1 * | 4/2003 | Ganz et al. ................... 606/41 |
| 5,830,213 | A | 11/1998 | Panescu et al. | 6,562,034 B2 | 5/2003 | Edwards et al. |
| 5,833,688 | A | 11/1998 | Sieben et al. | 6,572,578 B1 | 6/2003 | Blanchard |
| 5,836,874 | A * | 11/1998 | Swanson et al. ............ 600/374 | 6,572,610 B2 | 6/2003 | Kovalcheck et al. |
| 5,842,984 | A | 12/1998 | Avitall | 6,572,639 B1 | 6/2003 | Ingle et al. |
| 5,846,196 | A | 12/1998 | Siekmeyer et al. | 6,589,238 B2 | 7/2003 | Edwards et al. |
| 5,860,974 | A | 1/1999 | Abele | 6,689,130 B2 | 2/2004 | Arai et al. |
| 5,861,036 | A | 1/1999 | Godin | 6,695,764 B2 | 2/2004 | Silverman et al. |
| 5,863,291 | A | 1/1999 | Schaer | 6,712,814 B2 | 3/2004 | Edwards et al. |
| 5,871,483 | A | 2/1999 | Jackson et al. | 6,712,815 B2 | 3/2004 | Sampson et al. |
| 5,876,340 | A | 3/1999 | Tu et al. | 6,740,082 B2 | 5/2004 | Shadduck |
| 5,891,134 | A | 4/1999 | Goble et al. | 6,752,806 B2 | 6/2004 | Durgin et al. |
| 5,895,355 | A | 4/1999 | Schaer | 6,800,083 B2 * | 10/2004 | Hiblar et al. ................ 606/159 |
| 5,964,755 | A | 10/1999 | Edwards | 6,837,886 B2 | 1/2005 | Collins et al. |
| 5,976,129 | A | 11/1999 | Desai | 6,846,312 B2 | 1/2005 | Edwards et al. |
| 5,997,534 | A * | 12/1999 | Tu et al. ....................... 606/41 | 6,918,906 B2 | 7/2005 | Long |
| 6,006,755 | A * | 12/1999 | Edwards ..................... 128/898 | 6,953,469 B2 | 10/2005 | Ryan |
| 6,016,437 | A * | 1/2000 | Tu et al. ...................... 600/374 | 6,964,661 B2 * | 11/2005 | Rioux et al. ................... 606/41 |
| 6,027,499 | A | 2/2000 | Johnston et al. | 2001/0041887 A1 | 11/2001 | Crowley |
| 6,033,397 | A | 3/2000 | Laufer et al. | 2002/0177847 A1 | 11/2002 | Long |
| 6,041,260 | A | 3/2000 | Stern et al. | 2002/0183739 A1 | 12/2002 | Long |
| 6,044,846 | A | 4/2000 | Edwards | 2003/0158550 A1 * | 8/2003 | Ganz et al. ................... 606/41 |
| 6,053,913 | A | 4/2000 | Tu et al. | 2003/0181900 A1 | 9/2003 | Long |
| 6,056,744 | A | 5/2000 | Edwards | 2003/0181905 A1 | 9/2003 | Long |
| 6,071,277 | A | 6/2000 | Farley et al. | 2003/0216727 A1 | 11/2003 | Long |
| 6,073,052 | A | 6/2000 | Zelickson et al. | 2004/0087936 A1 | 5/2004 | Stern et al. |
| 6,086,558 | A | 7/2000 | Bower et al. | 2004/0215235 A1 | 10/2004 | Jackson et al. |
| 6,091,993 | A | 7/2000 | Bouchier et al. | 2004/0215296 A1 | 10/2004 | Ganz et al. |
| 6,091,995 | A | 7/2000 | Ingle et al. | 2005/0096713 A1 | 5/2005 | Starkebaum et al. |
| 6,092,528 | A | 7/2000 | Edwards | 2005/0171524 A1 | 8/2005 | Stern et al. |
| 6,095,966 | A | 8/2000 | Chornenky et al. | 2006/0095032 A1 | 5/2006 | Jackson et al. |
| 6,096,054 | A * | 8/2000 | Wyzgala et al. ............. 606/170 | 2006/0259028 A1 | 11/2006 | Utley et al. |
| 6,102,908 | A * | 8/2000 | Tu et al. ....................... 606/41 | 2006/0259029 A1 | 11/2006 | Utley et al. |
| 6,112,123 | A | 8/2000 | Kelleher et al. | 2006/0259030 A1 | 11/2006 | Utley et al. |
| 6,123,703 | A * | 9/2000 | Tu et al. ....................... 606/41 | 2006/0282071 A1 | 12/2006 | Utley et al. |
| 6,123,718 | A * | 9/2000 | Tu et al. ...................... 607/113 | 2007/0100333 A1 | 5/2007 | Jackson et al. |
| 6,138,046 | A | 10/2000 | Dalton | 2007/0118104 A1 | 5/2007 | Wallace et al. |
| 6,146,149 | A | 11/2000 | Daoud | 2007/0118106 A1 | 5/2007 | Utley et al. |
| 6,162,237 | A * | 12/2000 | Chan ........................... 606/198 | 2007/0135809 A1 | 6/2007 | Utley et al. |

FOREIGN PATENT DOCUMENTS

| | | |
|---|---|---|
| DE | 4303882 | 8/1994 |
| EP | 0105677 | 4/1984 |
| EP | 0115420 | 8/1984 |
| EP | 0139607 | 5/1985 |
| EP | 0251745 | 1/1988 |
| EP | 0608609 | 8/1994 |
| WO | WO 91/01773 | 2/1991 |
| WO | WO 92/10142 | 6/1992 |
| WO | WO 93/08755 | 5/1993 |
| WO | WO 94/10925 | 5/1994 |
| WO | WO 94/21165 | 9/1994 |
| WO | WO 94/21178 | 9/1994 |
| WO | WO 94/22366 | 10/1994 |
| WO | WO 94/26178 | 11/1994 |
| WO | WO 95/18575 | 7/1995 |
| WO | WO 95/19142 | 7/1995 |
| WO | WO 95/25472 | 9/1995 |
| WO | WO 96/00042 | 1/1996 |
| WO | WO 96/16606 | 6/1996 |
| WO | WO 96/29946 | 10/1996 |
| WO | WO 97/04702 | 2/1997 |
| WO | WO 97/06857 | 2/1997 |
| WO | WO 97/32532 | 9/1997 |
| WO | WO 97/43971 | 11/1997 |
| WO | WO 99/03413 | 1/1999 |
| WO | WO 99/35987 | 7/1999 |
| WO | WO 99/42046 | 8/1999 |
| WO | WO 99/55245 | 11/1999 |
| WO | WO 00/01313 | 1/2000 |
| WO | WO 00/59393 | 10/2000 |
| WO | WO 00/66021 | 11/2000 |
| WO | WO 01/35846 | 5/2001 |

OTHER PUBLICATIONS

Dallamagne, et al. Laparoscopic Nissen Fundoplication: Premliminary Surgical Laparoscopy and Endoscopy. 1991; 1(3):138-143.

Hinder, et al. The Technique of Laparoscopic Nissen Fundoplication. Surgical Laparoscopy and Endoscopy. 1992; 2(3):265-272.

Kaneko, et al. Physiological Laryngeal Pacemaker. Trans Am Soc. Artif Intern Organs. 1985; XXXI:293-296.

Karlstrom, et al. Ectopic Jejunal Pacemakers and Enterogastric Reflux Roux Gastrectomy: Effect of Intestinal Pacing. Surgery. 1989; 106(3):486-495.

Kelly, K.A. et al. Duodenal-Gastric Reflux and Slowed Gastric Emptying by Electrical Pacing of the Canine Duodenal Pacesetter Potential. Gastroenterology. 1977; 72(3):429-433.

Mugica, et al. Direct Diaphragm Stimulation. PACE. 1987; 10:252-256.

Mugica, et al., Preliminary Test of a Muscular Diaphragm Pacing System on Human Patients. Neurostimulation: An Overview, chapter 21. 1985; 263-279.

Reynolds, J.C. Influence of Pathophysiology, Severity, and Cost on the Medical Management of Gastroesophageal Reflux Disease. Am J. Health-Syst Phar. 1996; 53(22sul3):S5-S12.

Rice, et al. Endoscopic Paranasal Sinus Surgery. Chapter 5, Functional Endoscopic Paranasal Sinus Surgery, The Technique of Messerklinger. Raven Press. 1988; 75-102.

Rice, et al. Endoscopic Paranasal Sinus Surgery, Chapter 6, Total Endoscopic Sphenoethmoldectomy. The Technique of Wigand. Raven Press. 1988; 103-125.

Salameh et al; An Animal Model Study to Clarify and Investigate Endoscopic Tissue Coagulation by Using a New Monopolar Device. Gastrointestinal Endoscopy; 2004; 59 (1): 107-112.

Urshel, J.D. Complications of Antireflux Surgery. Am J surg. 1993; 166(1):68-70.

Shadduck, J.H. U.S. Pat. App. # 11/469,816 entitled "Surgical Instruments And Techniques For Treating Gastro-Esophageal Reflux Disease," filed Sep. 1, 2006, (SLG# 10077-713.301).

* cited by examiner

DEVICES AND METHODS FOR TREATMENT OF LUMINAL TISSUE

CROSS-REFERENCE

This application is a divisional application of Ser. No. 10/754,444, filed Jan. 9, 2004, now U.S. Pat. No. 7,150,745, which is incorporated herein by reference in its entirety, and to which application we claim priority under 35 USC § 121.

BACKGROUND OF THE INVENTION

1. Field of the Invention

The present invention relates generally to medical devices and methods. More particularly, the invention is directed to devices and methods for treating the esophagus and other interior tissue regions of the body.

The human body has a number of internal body lumens or cavities located within, many of which have an inner lining or layer. These inner linings can be susceptible to disease. In some cases, surgical intervention can be required to remove the inner lining in order to prevent the spread of disease to otherwise healthy tissue located nearby.

Those with persistent problems with or inappropriate relaxation of the lower esophageal sphincter can develop a condition known as gastroesophageal reflux disease, manifested by classic symptoms of heartburn and regurgitation of gastric and intestinal content. The causative agent for such problems may vary. Patients with severe forms of gastroesophageal reflux disease, no matter what the cause, can sometimes develop secondary damage of the esophagus due to the interaction of gastric or intestinal contents with esophageal cells not designed to experience such interaction.

The esophagus is composed of three main tissue layers; a superficial mucosal layer lined by squamous epithelial cells, a middle submucosal layer and a deeper muscle layer. When gastroesophageal reflux occurs, the superficial squamous epithelial cells are exposed to gastric acid, along with intestinal bile acids and enzymes. This exposure may be tolerated, but in some cases can lead to damage and alteration of the squamous cells, causing them to change into taller, specialized columnar epithelial cells. This metaplastic change of the mucosal epithelium from squamous cells to columnar cells is called Barrett's esophagus, named after the British surgeon who originally described the condition.

Barrett's esophagus has important clinical consequences, since the Barrett's columnar cells can, in some patients, become dysplastic and then progress to a certain type of deadly cancer of the esophagus. The presence of Barrett's esophagus is the main risk factor for the development of adenocarcinoma of the esophagus.

Accordingly, attention has been focused on identifying and removing this abnormal Barrett's columnar epithelium in order to mitigate more severe implications for the patient. Examples of efforts to properly identify Barrett's epithelium, or more generally Barrett's esophagus, have included conventional visualization techniques known to practitioners in the field. Although certain techniques have been developed to characterize and distinguish such epithelium cells, such as disclosed in U.S. Pat. Nos. 5,524,622 and 5,888,743, there has yet to be shown safe and efficacious means of accurately removing undesired growths of this nature from portions of the esophagus to mitigate risk of malignant transformation.

Devices and methods for treating abnormal body tissue by application of various forms of energy to such tissue have been described, and include laser treatment, microwave treatment, radio frequency ablation, ultrasonic ablation, photodynamic therapy using photo sensitizing drugs, argon plasma coagulation, cryotherapy, and x-ray. These methods and devices have been deficient however, since they do not allow for precise control of the depth of penetration of the energy means. This is a problem since uncontrolled energy application can penetrate too deeply into the esophageal wall, beyond the mucosa and submucosal layers, into the muscularis externa, potentially causing esophageal perforation, stricture or bleeding. In addition, most of these methods and devices treat only a small portion of the abnormal epithelium at one time, making treatment of Barrett's time consuming, tedious, and costly.

For example, U.S. Pat. No. 6,112,123 describes a device and method for ablating tissue in the esophagus. The device and method, however, do not adequately control the application of energy to effect ablation of tissue to a controlled depth.

In many therapeutic procedures performed on layered tissue structures, it may be desirable to treat or affect only superficial layer(s) of tissue, while preserving intact the function of deeper layers. In the treatment of Barrett's esophagus, the consequences of treating too deeply and affecting layers beneath the mucosa can be significant. For example, treating too deeply and affecting the muscularis can lead to perforation or the formation of strictures. In the treatment of Barrett's esophagus, it may be desired to treat the innermost mucosal layer, while leaving the intermediate submucosa intact. In other situations, it may be desired to treat both the mucosal and submucosa layers, while leaving the muscularis layer intact.

One device which solves this problem is disclosed in U.S. Pat. No. 6,551,310 B1. The abovementioned patent discloses a device and method of treating abnormal tissue utilizing an expandable balloon with an array of closely spaced electrodes to uniformly treat a desired region of tissue. With the electrodes closely spaced in an array and for the same energy delivery parameters, the depth of ablation is limited to a distance that is related to the size and spacing between the electrodes, facilitating a uniform and controlled ablation depth across the treatment area. However, because the diameter of the esophagus and other lumens vary from patient to patient, the spacing between the electrodes (electrode density) will also vary as the balloon expands to accommodate the different sizes. Therefore, in order to keep the electrode density and corresponding ablation depth at the desired constant, a number of different catheters having a range of balloon diameters must be available and chosen appropriately to fit the corresponding size of the lumen.

Therefore, it would be advantageous to have devices and methods for complete treatment of an inner layer of luminal tissue to a desired depth while ensuring that the deeper layers are unharmed. In particular, it would be desirable to provide an electrode deployment device that can expand to uniformly engage the surface of a lumen and maintain a constant electrode density as the device is expanded. At least some of these objectives will be met by the present invention.

2. Description of the Background Art

U.S. Pat. Nos. 5,524,622; 5,888,743; 6,112,123; and 6,551,310 have been described above. Other patents of interest include U.S. Pat. Nos. 4,658,836; 4,674,481; 4,776,349; 4,949,147; 4,955,377; 4,979,948; 5,006,119; 5,010,895; 5,045,056; 5,117,828; 5,151,100; 5,277,201; 5,428,658; 5,443,470; 5,454,809; 5,456,682; 5,496,271; 5,505,730; 5,514,130; 5,542,916; 5,549,661; 5,566,221; 5,562,720; 5,569,241; 5,599,345; 5,621,780; 5,648,278; 5,713, 942; 5,730,128; 5,748,699; 5,769,846; 5,769,880; 5,836,874; 5,846,196; 5,861,036; 5,891,134; 5,895,355; 5,964,755; 6,006,755; 6,033,397; 6,041,260; 6,053,913; 6,071,277; 6,073,052; 6,086,558; 6,091,993; 6,092,528; 6,095,966; 6,102,908; 6,123,703; 6,123,718; 6,138,046; 6,146,149; 6,238,392; 6,254,598; 6,258,087; 6,273,886; 6,321,121; 6,355,031; 6,355,032; 6,363,937; 6,383,181; 6,394,949; 6,402,744; 6,405,732; 6,415,016; 6,423,058; 6,423,058; 6,425,877; 6,428,536; 6,440,128; 6,454,790; 6,464,697; 6,448,658; 6,535,768; 6,572,639; 6,572,578; and 6,589,238. Patent publications of interest include U.S. Ser. No. 2001/0041887; U.S. Ser. No. 2002/0013581; U.S. Ser. No. 2002/0143325 A1; U.S. Ser. No. 2002/0156470; U.S. Ser. No. 2002/0183739; U.S. Ser. No. 2003/0045869 A1; U.S. 2003/0009165 A1.

BRIEF SUMMARY OF THE INVENTION

According to the present invention, an electrode deployment device for treatment of tissue in a body lumen comprises a plurality of electrodes having a pre-selected electrode density arranged on the surface of a dimensionally stable support. An expansion member, such as an inflatable balloon, selectively exposes a portion of the electrode surface while a remaining portion remains shielded. Thus, the support can be expanded to engage the needed area of electrodes against targeted luminal tissue while maintaining the electrode density.

Although the following description will focus on embodiments configured for treatment of the esophagus, other embodiments may be used to treat any other suitable lumen in the body. In particular, the electrode deployment devices and methods of the present invention may be used whenever uniform delivery of energy is desired to treat a controlled depth of tissue in a lumen or cavity of the body, especially where such body structures may vary in size. Therefore, the following description is provided for exemplary purposes and should not be construed to limit the scope of the invention.

In many embodiments, the support may be comprised of a flexible, non-distensible backing. For example, the backing may comprise of a thin, rectangular sheet of a polymer material such as polyimide, polyester or other flexible thermoplastic or thermosetting polymer film, polymer covered materials, or other nonconductive materials. The backing may also be comprised of an electrically insulating polymer, with an electro-conductive material, such as copper, deposited onto a surface. For example, an electrode pattern can be etched into the material to create an array of electrodes. In some embodiments, the support is spirally furled about an axis of the expansion member. The electrode pattern may be aligned in axial or traverse direction across the backing, formed in a linear or non-linear parallel array or series of bipolar pairs, or other suitable pattern. Depending on the desired treatment effect, the electrodes may be arranged to control the depth and pattern of treatment. For treatment of esophageal tissue, the electrodes typically have a width from 0.1 mm to 3 mm, preferably from 0.1 mm to 0.3 mm, and are spaced apart by a distance in the range from 0.1 mm to 3 mm, typically from 0.1 mm to 0.3 mm.

The expandable member may comprise any material or configuration. In some embodiments, for example, the expansion member comprises an inflatable balloon that is tapered at both ends. A balloon-type expansion member may be elastic, or optionally comprise a non-distensible bladder having a shape and a size in its fully expanded form that will extend in an appropriate way to the tissue to be contacted.

Additional embodiments may comprise a basket, plurality of struts, an expandable member with a furled and an unfurled state, one or more springs, foam, backing material that expands to an enlarged configuration when unrestrained, and the like.

In many aspects of the invention, the support is furled around the balloon so that the electrode-exposed surface of the support unfurls as the balloon is inflated. For example, the support may be coiled into a loop and placed around an expandable balloon, so that a first end of the support is furled around the balloon overlapping the second end of the support. Some embodiments further include one or more elastic members that are attached to the second end and another point on the support to keep the backing constrained until being unfurled. As the balloon expands, the elastic members allow the support to unfurl and further expose additional electrodes that had previously been shielded by the overlapping portion of the support.

In another embodiment, the support is attached at its first end to a balloon, and a second end is unattached and furled around the balloon overlapping the first end of the support. As the balloon expands, the support unfurls and exposes additional electrodes that had previously been shielded by the overlapping portion of the support. Alternatively, the support is attached at its midpoint to the surface of the balloon and the ends of the support are furled in opposite directions around the balloon In one aspect of the invention, a first support is attached at its midpoint to an expandable balloon so that the ends of the first support furl around the balloon in opposite directions. A second support is also attached at its midpoint to the balloon opposite from the first support, the ends of the second support also being furled in opposite directions around the balloon and overlapping the ends of the first support. Some embodiments further include one or more elastic members coupled to the first and second supports. As the balloon expands, the elastic members allow the supports to unfurl with respect to each other and further expose additional electrodes of the first support that had previously been shielded by the overlapping portion of the second support.

In some embodiments, the support is spirally furled inside a container having a slot down its axis through which one end of the furled support can pass. The container may comprise of a tubular-shaped, semi-rigid material, such as a plastic. A balloon surrounds a portion of the outside surface of the container, avoiding the opening provided by the axial slot. The support is partially unfurled from the container, through the slot and around the circumference of the balloon until it again reaches the slot in the container where it is attached at one end. Alternatively, the support may be attached to the balloon at a location proximal to the slot. When the balloon expands, the support unfurls from the container, exposing additional electrodes to compensate for the increased surface area of the balloon, and maintaining the constant electrode density on the surface of the support. Optionally, in some embodiments, the support is folded into a plurality of pleats inside the container. In further embodiments, the support is attached to a shaft and is furled around the shaft inside the container. The shaft, for example, may comprise an elongate, handheld rod of a flexible material such as a metallic wire. Optionally, the device may further include a torsion spring coupled to the shaft.

In another aspect of the invention, the expansion member comprises a spiral spring. The spring, for example, may comprise of a wire, series of wires, or strip or sheet of spring temper or superelastic memory material, such as 316 stainless steel or nitinol, that provides an unwinding force or constant stress or force while expanding from a compressed state. In some embodiments, the support is attached to the outer surface of the spring support. Optionally, the apparatus may further comprise a shaft that is coupled to the spring.

In yet another aspect, the expansion member comprises a balloon having an adhesive applied to selected areas of the balloon's outside surface, so that the balloon can be folded over at one or more of the adhesive areas to form one or more creases. As the balloon expands, the creases expand to expose additional electrodes of the support that surrounds the balloon In another embodiment of the invention, an electrode deployment apparatus for treating tissue in a body lumen comprises: a shaft; a support attached at one end to the distal end of the shaft and spirally furled about the shaft; a balloon slidably received on the shaft axially proximal to the support, wherein the balloon and support are retained in a sheath so that they may be advanced past the sheath once the apparatus is positioned at a treatment area, and wherein the balloon is further advanced to the distal end of the shaft to expand the support.

In another aspect of the invention, an electrode deployment apparatus comprising: a plurality of electrodes arranged on a surface of a support at a pre-selected electrode density; an expansion member coupled to expand the support to selectively expose a portion of the electrode surface while shielding a remaining portion and maintaining the electrode density; and a transesophageal catheter, wherein the expansion member is disposed at a distal end of the catheter. The apparatus may further comprise a RF power source coupled to the plurality of electrodes. In some embodiments, the apparatus may also include a multiplexer and/or temperature sensor coupled to the plurality of electrodes. Optionally, the apparatus might also have a control device coupled to the plurality of electrodes, the control device providing controlled positioning of the expandable member.

In still another aspect of the invention, an electrode deployment apparatus for treatment of tissue in a human esophagus includes: a plurality of electrodes arranged on a surface of a support at a pre-selected electrode density; and an expansion member coupled to expand the support to engage the electrode surface to a wall of the esophagus while maintaining the electrode density. The electrodes may be arranged in a parallel pattern, and have a spacing between them of up to 3 mm. The support may comprise a non-distensible electrode backing. In some embodiments, the expandable member may comprise an inflatable balloon.

In many embodiments of the above electrode deployment apparatus, the support is furled at least partially around the balloon, so that the support unfurls as the balloon is inflated. The support may further be attached at one end to the surface of the balloon with the second end of the support being furled around the balloon. Alternatively, in some embodiments, the support is attached at its midpoint to the surface of the balloon, a first and second end of the support furled in opposite directions around the balloon. Optionally, the support may be sized so that the ends of the support do not overlap, thereby keeping the exposed area of electrodes constant during expansion of the balloon.

In one aspect of the invention, a method for deploying electrodes to treat tissue in a body lumen comprises positioning an array of electrodes having a pre-selected electrode density within the body lumen, and exposing an area of the array sufficient to engage a wall of the lumen while maintaining the electrode density, wherein the size of the exposed area may vary depending on the size of the body lumen. In many embodiments, positioning the array comprises transesophageally delivering the array to a treatment area within the esophagus. For example, the array may be advanced via a catheter carrying the array through the esophagus. Some embodiments further include applying radiofrequency energy to tissue of the body lumen through the electrodes. Optionally, such embodiments may also include applying bipolar radiofrequency energy through a multiplicity of bipolar electrode pairs in the array. The electrodes in the array may be parallel, and have a width in the range from 0.1 mm to 3 mm, and be spaced-apart by a distance in the range from 0.1 mm to 3 mm. Generally, the total radiofrequency energy delivered to the esophageal tissue will be in the range from 1 joules/cm$^2$ to 50 joules/cm$^2$, usually being from 5 joules/cm$^2$ to 50 joules/cm$^2$. In many embodiments, the array comprises a non-distensible, electrode support that is furled about an axis of the expansion member, wherein expanding comprises unfurling the support to selectively expose a portion of the available electrode area. In most cases, unfurling comprises expanding an expansion member such as an inflatable balloon within the furled support In one aspect of the invention, the above method for deploying electrodes to treat tissue in a body lumen further comprises: furling the support about an axis so that its ends overlap each other; coupling an elastic member to the support to retain the support from unfurling freely; placing the balloon within the circumference of the furled support; advancing the support assembly to a desired treatment region; and expanding the balloon to deploy the backing against a wall of the lumen.

In yet another embodiment of the invention, a method for deploying electrodes to treat tissue in a body lumen comprises: furling a support with an array of electrodes having a pre-selected density about the distal end of a shaft having a balloon slidably received on the shaft proximal to the support; positioning the balloon and support inside a sheath; positioning the sheath assembly near a treatment area; advancing the balloon and support past the sheath; advancing the balloon to the distal end of the shaft; positioning the balloon and support at the treatment area; and expanding the balloon to deploy the backing against the lumen.

DETAILED DESCRIPTION OF THE INVENTION

In various embodiments, the present invention provides devices and methods for treating, at a controlled and uniform depth, the inner lining of a lumen or cavity within a patient. It will be appreciated that the present invention is applicable to a variety of different tissue sites and organs, including but not limited to the esophagus. A treatment apparatus including an energy delivery device comprising an expandable electrode array is provided. At least a portion of the delivery device is positioned at the tissue site, where the electrode array is expanded to contact the tissue surface. Sufficient energy is delivered from the electrode array to impart a desired therapeutic effect, such as ablation as described below, to a discreet layer of tissue.

Figure 1:
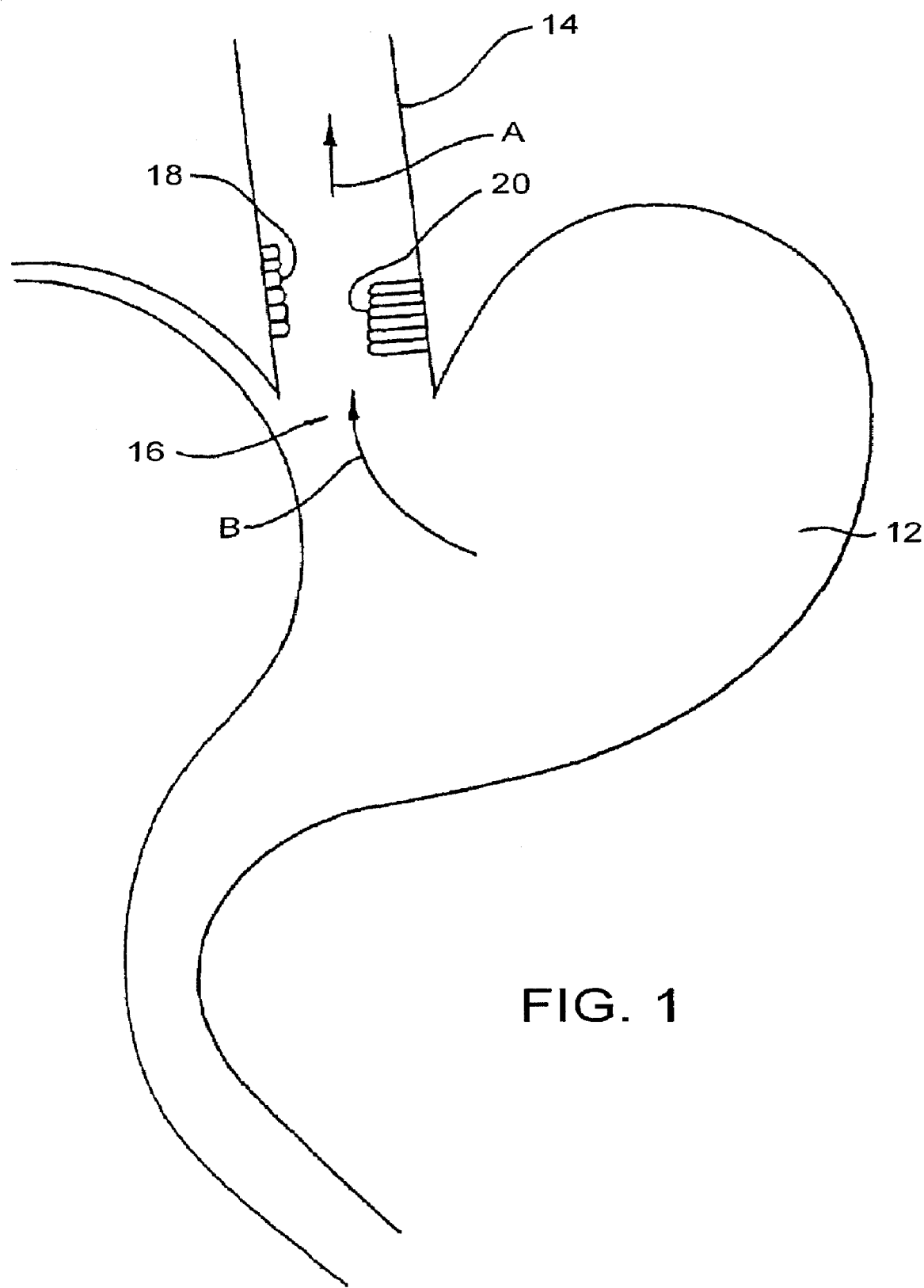
FIG. 1 is a schematic view of portions of an upper digestive tract in a human.

Certain disorders can cause the retrograde flow of gastric or intestinal contents from the stomach 12, into the esophagus 14, as shown by arrows A and B in FIG. 1. Although the causation of these problems are varied, this retrograde flow may result in secondary disorders, such as Barrett's esophagus, which require treatment independent of and quite different from treatments appropriate for the primary disorder—such as disorders of the lower esophageal sphincter 16. Barrett's esophagus is an inflammatory disorder in which the stomach acids, bile acids and enzymes regurgitated from the stomach and duodenum enter into the lower esophagus causing damage to the esophageal mucosa. When this type of retrograde flow occurs frequently enough, damage may occur to esophageal epithelial cells 18. In some cases the damage may lead to the alteration of the squamous cells, causing them to change into taller specialized columnar epithelial cells 20. This metaplastic change of the mucosal epithelium from squamous cells to columnar cells is called Barrett's esophagus. Although some of the columnar cells may be benign, others may result in adenocarcinoma.

In one aspect, the present invention provides devices and methods for treating columnar epithelium of selected sites of the esophagus in order to mitigate more severe implications for the patient. In many therapeutic procedures according to the present invention, the desired treatment effect is ablation of the tissue. The term "ablation" as used herein means thermal damage to the tissue causing tissue or cell necrosis. However, some therapeutic procedures may have a desired treatment effect that falls short of ablation, e.g. some level of agitation or damage that is imparted to the tissue to inure a desired change in the cellular makeup of the tissue, rather than necrosis of the tissue. With the present invention, a variety of different energy delivery devices can be utilized to create a treatment effect in a superficial layer of tissue, while preserving intact the function of deeper layers, as described hereafter.

Cell or tissue necrosis can be achieved with the use of energy, such as radiofrequency energy, at appropriate levels to accomplish ablation of mucosal or submucosal level tissue, while substantially preserving muscularis tissue. Such ablation is designed to remove the columnar growths 20 from the portions of the esophagus 14 so affected.

Figure 2:
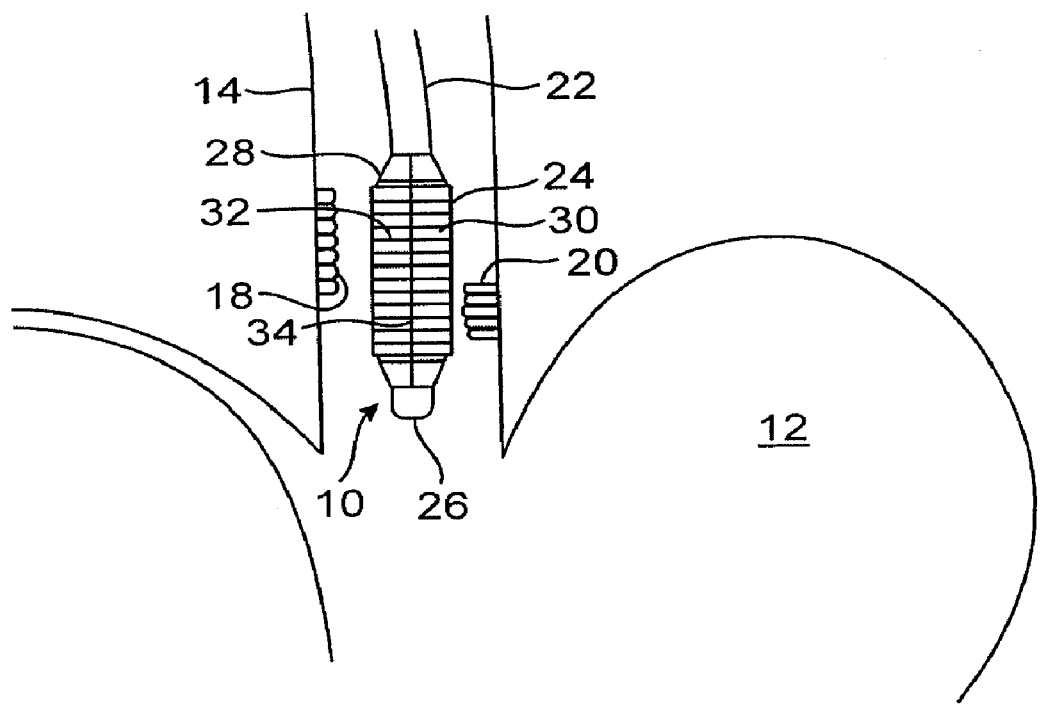
FIG. 2 is a schematic view of a device of the invention, in a compressed mode, within an esophagus
Figure 3:
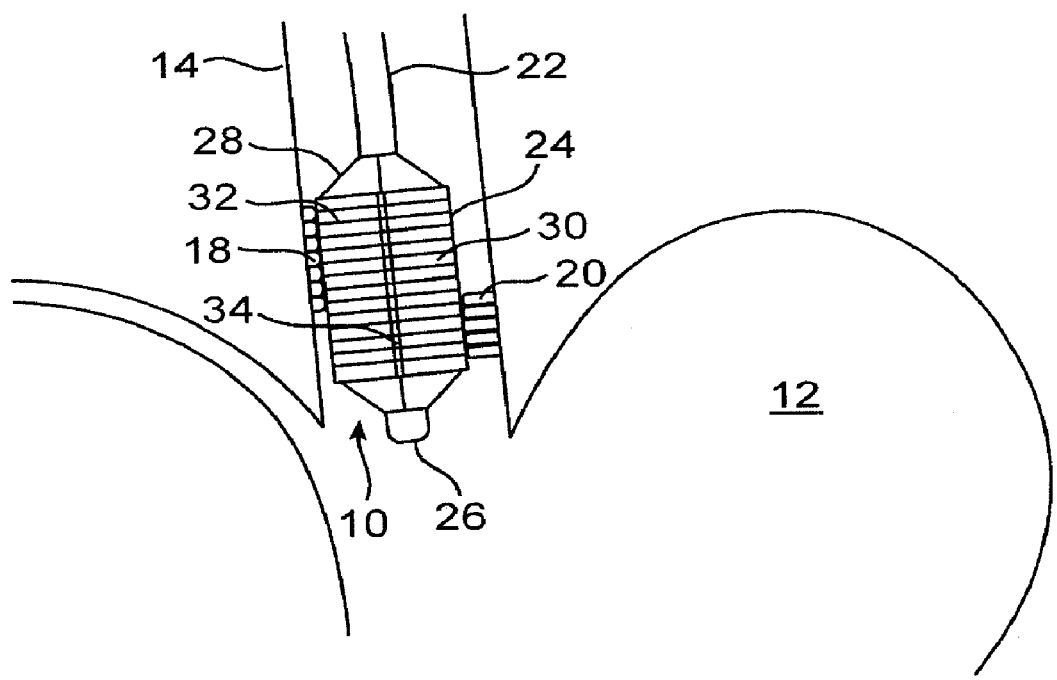
FIG. 3 is a schematic view of a device of the invention, in an expanded mode, within an esophagus

As illustrated in FIGS. 2 and 3, a treatment apparatus 10 constructed in accordance with the principles of the present invention, includes an elongated catheter sleeve 22, that is configured to be inserted into the body in any of various ways selected by the medical provider. Apparatus 10 may be placed, (i) endoscopically, e.g. through esophagus 14, (ii) surgically or (iii) by other means. As shown in FIG. 2, the apparatus is delivered to the treatment area within the esophagus while in a non-expanded state. This low-profile configuration allows for ease-of-access to the treatment site without discomfort or complications to the patient. Proper treatment of the tissue site, however, requires the apparatus to expand to the diameter of the esophagus, as illustrated in FIG. 3. Once expanded, the apparatus can uniformly deliver treatment energy to the desired tissue site.

When an endoscope (not shown) is used, catheter sleeve 22 can be inserted in the lumen of the endoscope, or catheter sleeve 22 can be positioned along the outside of the endoscope. Alternately, an endoscope may be used to visualize the pathway that catheter 22 should follow during placement. As well, catheter sleeve 22 can be inserted into esophagus 14 after removal of the endoscope.

An electrode support 24 is provided and can be positioned at a distal end 26 of catheter sleeve 22 to provide appropriate energy for ablation as desired. Electrode support 24 has a plurality of electrode area segments 32 attached to the surface of the support. The electrodes 32 can be configured in an array 30 of various patterns to facilitate a specific treatment by controlling the electrode size and spacing (electrode density). In various embodiments, electrode support 24 is coupled to an energy source configured for powering array 30 at levels appropriate to provide the selectable ablation of tissue to a predetermined depth of tissue.

In many embodiments, the support 24 may comprise a flexible, non-distensible backing. For example, the support 24 may comprise of a thin, rectangular sheet of polymer materials such as polyimide, polyester or other flexible thermoplastic or thermosetting polymer film. The support 24 may also comprise polymer covered materials, or other nonconductive materials. Additionally, the backing may include an electrically insulating polymer, with an electroconductive material, such as copper, deposited onto a surface so that an electrode pattern can be etched into the material to create an array of electrodes Electrode support 24 can be operated at a controlled distance from, or in direct contact with the wall of the tissue site. This can be achieved by coupling electrode support 24 to an expandable member 28, which has a configuration that is expandable in the shape to conform to the dimensions of the expanded (not collapsed) inner lumen of the tissue site or structure, such as the human lower esophageal tract.

Suitable expandable members 28 include but are not limited to a balloon, compliant balloon, balloon with a tapered geometry, basket, plurality of struts, an expandable member with a furled and an unfurled state, one or more springs, foam, bladder, backing material that expands to an expanded configuration when unrestrained, and the like.

Expandable member 28 can also be utilized to place electrode support 24, as well as to anchor the position of electrode support 24. This can be achieved with expandable member 28 itself, or other devices that are coupled to member 28 including but not limited to an additional balloon, a plurality of struts, a bladder, and the like.

In many embodiments, electrode support 24 is utilized to regulate and control the amount of energy transferred to the tissue at a tissue site such as the inner wall of a lumen. Expandable member 28 can be bonded to a portion of catheter sleeve 22 at a point spaced from distal end 26. Electrode support 24 may be furled at least partially around the outside circumference of expandable member 28 so that when expansion member 28 expands, support 24 adapts to the changing circumference while maintaining a constant electrode density per unit area. Energy is transferred from the catheter sleeve 22 to the electrode support 24 on expandable member 28. By way of illustration, one type of energy distribution that can be utilized is disclosed in U.S. Pat. No. 5,713,942, incorporated herein by reference, in which an expandable balloon is connected to a power source, which provides radio frequency power having the desired characteristics to selectively heat the target tissue to a desired temperature In one embodiment, catheter sleeve 22 includes a cable that contains a plurality of electrical conductors surrounded by an electrical insulation layer, with an electrode support 24 positioned at distal end 26. A positioning and distending device can be coupled to catheter sleeve 22. The positioning and distending device can be configured and sized to contact and expand the walls of the body cavity in which it is placed, by way of example and without limitation, the esophagus. The positioning and distending device can be at different positions of electrode support 24, including but not limited to its proximal and/or distal ends, and also at its sides.

Figure 10:
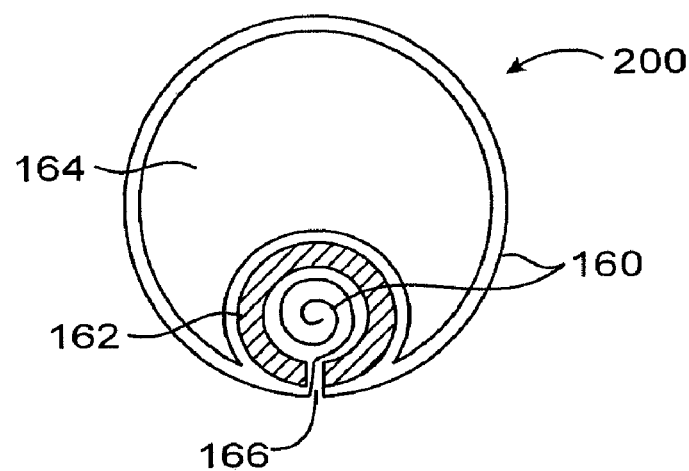
FIG. 10 is an enlarged cross-sectional view of a device of the invention in an expanded configuration.

As shown in FIGS. 2 and 3, in an embodiment of the present invention, electrode support 24 can be positioned so that energy is uniformly applied to all or a portion of the inner circumference of the lumen where treatment is desired. This can be accomplished by first positioning apparatus 10 to the treatment area in a compressed configuration with the electrode support 24 furled around the outside circumference of expandable member 28. Once the apparatus is advanced to the appropriate site, expandable member 28 is inflated, which unfurls electrode support 24 to engage the internal wall of the lumen. In some embodiments, additional electrode support may unfurl from slot 34, shown in greater detail as slot 166 in FIGS. 10 through 12, where the electrode support was previously shielded prior to expansion. The desired treatment energy may then be delivered to the tissue as necessary. As illustrated in FIG. 3, the electrode support 24 uniformly engages the inner wall of the lumen with an array of electrodes 30 having a constant density so that the energy is uniformly applied to all or a portion of the circumference of the inner lumen of the esophagus or other tissue site One way to ensure that the energy is uniformly applied to the circumference of the inner lumen of the esophagus is the use of a vacuum or suction element to "pull" the esophageal wall, or other tissue site, against the outside circumference of expandable member 28. This suction element may be used alone to "pull" the esophageal wall into contact with electrode support 24, carried on or by catheter sleeve 22 without the use of expandable member 28, or in conjunction with expandable member 28 to ensure that the wall is in contact with electrode support 24 while carried on the outside of expandable member 28. This same result can be achieved with any of the electrode supports 24 utilized, and their respective forms of energy, with respect to expandable member 28 so that the energy is uniformly applied.

Electrode support 24 can deliver a variety of different types of energy including but not limited to, radio frequency, microwave, ultrasonic, resistive heating, chemical, a heatable fluid, optical including without limitation, ultraviolet, visible, infrared, collimated or non collimated, coherent or incoherent, or other light energy, and the like. It will be appreciated that the energy, including but not limited to optical, can be used in combination with one or more sensitizing agents.

The energy source may be manually controlled by the user and is adapted to allow the user to select the appropriate treatment time and power setting to obtain a controlled depth of ablation. The energy source can be coupled to a controller (not shown), which may be a digital or analog controller for use with the energy source, including but not limited to an RF source, or a computer with software. When the computer controller is used it can include a CPU coupled through a system bus. The system may include a keyboard, a disk drive, or other non-volatile memory system, a display and other peripherals known in the art. A program memory and a data memory will also be coupled to the bus.

The depth of treatment obtained with apparatus 10 can be controlled by the selection of appropriate treatment parameters by the user as described in the examples set forth herein. One important parameter in controlling the depth of treatment is the electrode density of the array 30. As the spacing between electrodes decreases, the depth of treatment of the affected tissue also decreases. Very close spacing of the electrodes assures that the current and resulting ohmic heating is limited to a very shallow depth so that injury and heating of the submucosal layer are minimized. For treatment of esophageal tissue using RF energy, it may be desirable to have a width of each RF electrode to be no more than, (i) 3 mm, (ii) 2 mm, (iii) 1 mm (iv) 0.5 mm or (v) 0.3 mm (vi) 0.1 mm and the like. Accordingly, it may be desirable to have a spacing between adjacent RF electrodes to be no more than, (i) 3 mm, (ii) 2 mm, (iii) 1 mm (iv) 0.5 mm or (v) 0.3 mm (vi) 0.1 mm and the like. The plurality of electrodes can be arranged in segments, with at least a portion of the segments being multiplexed. An RF electrode between adjacent segments can be shared by each of adjacent segments when multiplexed.

Figure 6A:
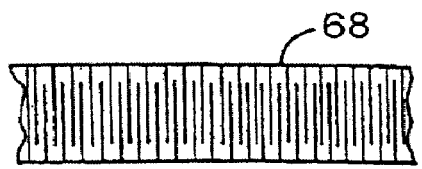
FIG. 6 shows the electrode patterns of the device of FIG. 3.
Figure 6B:
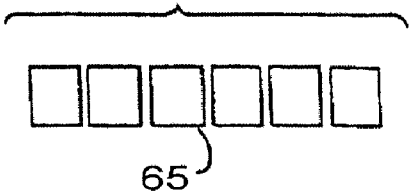
Figure 6C:
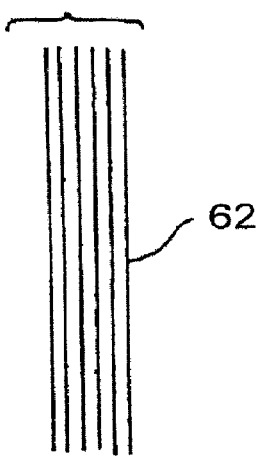
Figure 7A:
FIG. 7 shows the electrode patterns that may be used with a device of the invention.
Figure 7B:
Figure 7D:
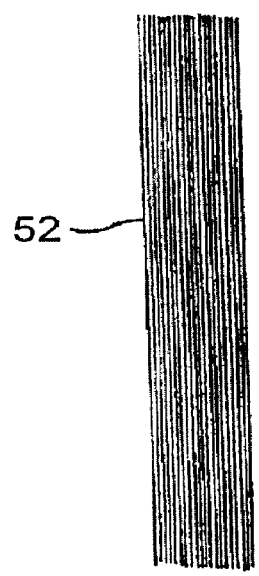
Figure 7C:
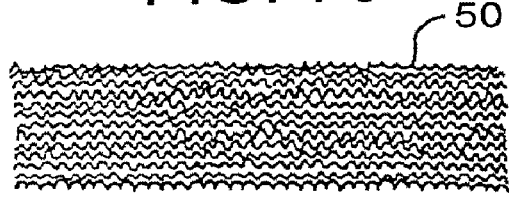

The electrode patterns of the present invention may be varied depending on the length of the site to be treated, the depth of the mucosa and submucosa, in the case of the esophagus, at the site of treatment and other factors. The electrode pattern 30 may be aligned in an axial or traverse direction across the electrode support 24, or formed in a linear or non-linear parallel matrix or series of bipolar pairs or monopolar electrode. One or more different patterns may be coupled to various locations of expandable member 28. For example, an electrode array, as illustrated in FIGS. 6(*a*) through 6(*c*), may comprise a pattern of bipolar axial interlaced finger electrodes 68, six bipolar rings 62 with 2 mm separation, or monopolar rectangles 65 with 1 mm separation. Other suitable RF electrode patterns which may be used include, without limitation, those patterns shown in FIGS. 7(*a*) through 7(*d*) as 46, 48, 50 and 52, respectively. Pattern 46 is a pattern of bipolar axial interlaced finger electrodes with 0.3 mm separation. Pattern 48 includes monopolar bands with 0.3 mm separation. Pattern 52 includes bipolar rings with 0.3 mm separation. Pattern 50 is electrodes in a pattern of undulating electrodes with 0.2548 mm separation.

A probe sensor may also be used with the system of the present invention to monitor and determine the depth of ablation. In one embodiment, one or more sensors (not shown), including but not limited to thermal and the like, can be included and associated with each electrode segment 32 in order to monitor the temperature from each segment and then control the energy delivery to that segment. The control can be by way of an open or closed loop feedback system. In another embodiment, the electroconductive member can be configured to permit transmission of microwave energy to the tissue site. Treatment apparatus 10 can also include steerable and directional control devices, a probe sensor for accurately sensing depth of ablation, and the like.

Figure 4:
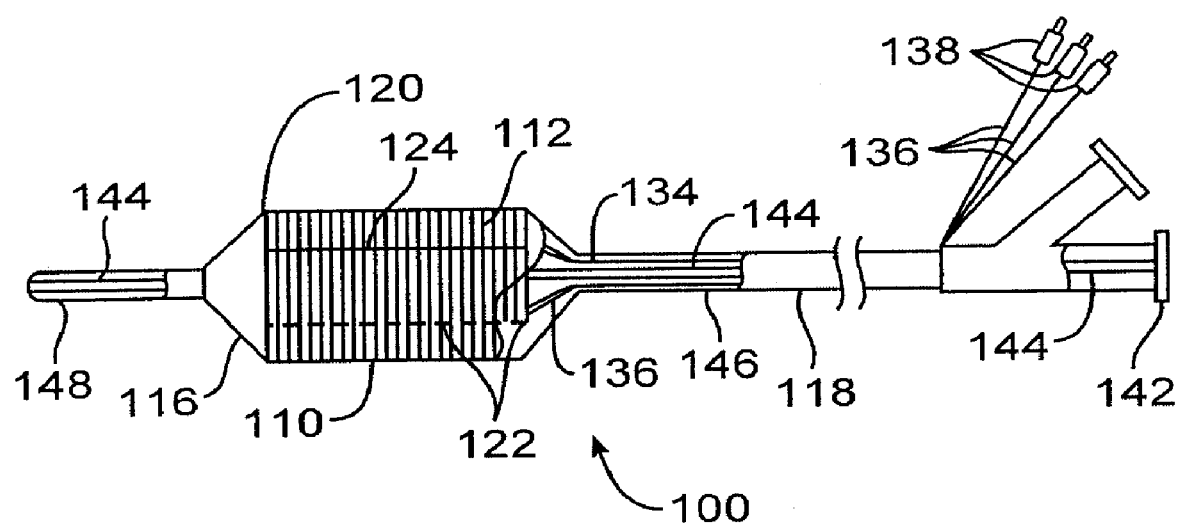
FIG. 4 is a schematic view of another embodiment of a device of the invention.

Referring to FIG. 4, one embodiment of the invention comprises an electrode deployment device 100 having an electrode support 110 furled around the outside of an inflatable balloon 116 that is mounted on a catheter sleeve 118. Support 110 has an electrode array 112 etched on its surface, and is aligned between edges 120 that intersect the taper region located at the distal and proximal ends of balloon 116. Support 110 is attached at a first end 122 to balloon 116 with an adhesive. The second end 124 of the support is furled around the balloon, overlapping the first end 122.

Figure 5:
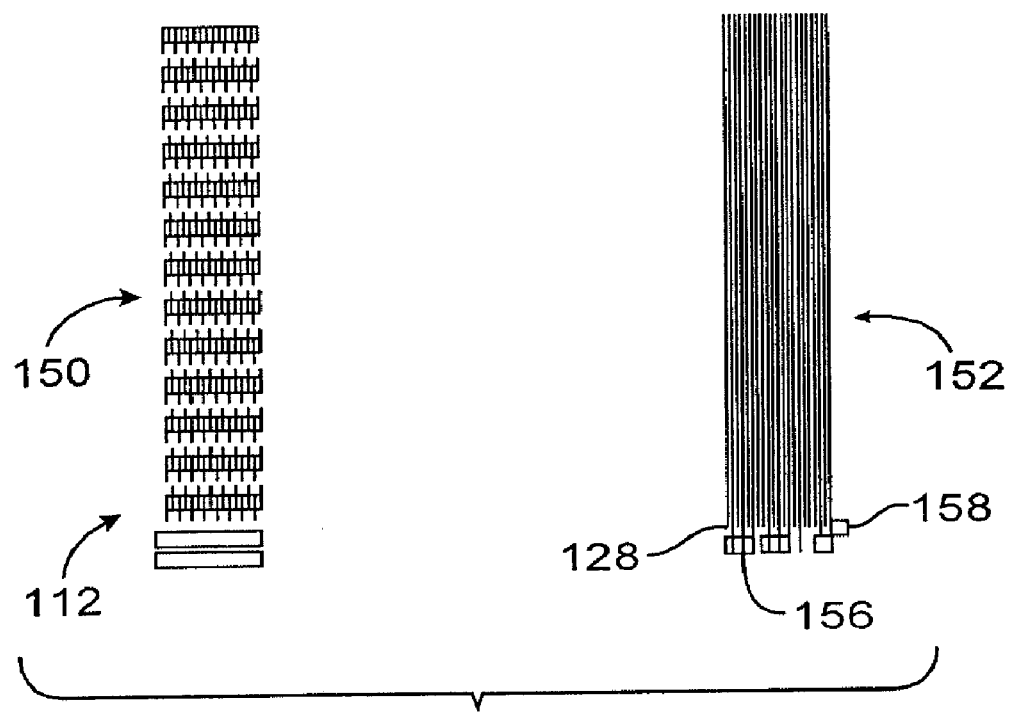
FIG. 5 shows a top view and a bottom view of an electrode pattern of the device of FIG. 4.

FIG. 5 shows a bottom view 150 and a top view 152 of the electrode array 112 of support 110. In this embodiment, the array 112 has 20 parallel bars, 0.25 mm wide, separated by gaps of 0.3 mm. The bars on the circuit form twenty complete continuous rings around the circumference of balloon 116. Electrode array 112 can be etched from a laminate consisting of copper on both sides of a polyimide substrate. One end of each copper bar has a small plated through hole 128, which allows signals to be passed to these bars from 1 of 2 copper junction blocks 156 and 158, respectively, on the back of the laminate. One junction block 156 is connected to all of the even numbered bars, while the other junction block 158 is connected to all of the odd numbered bars.

As shown in FIGS. 4 and 5, each junction block 156 and 158 is then wired to a bundle of AWG wires 134. The wiring is external to balloon 116, with the distal circuit wires affixed beneath the proximal circuit. Upon meeting the catheter sleeve of the device, these bundles 134 can be soldered to three litz wire bundles 136. One bundle 136 serves as a common conductor for both circuits while the other two bundles 136 are wired individually to each of the two circuits. The litz wires are encompassed with heat shrink tubing along the entire length of the catheter sleeve 118 of the device. Upon emerging from the proximal end of the catheter sleeve, each of these bundles 136 is individually insulated with heat shrink tubing before terminating to a mini connector plug 138. Under this configuration, power can be delivered to either or both of the two bundles so that treatment can be administered to a specific area along the array.

They connector 142 at the proximal end of the catheter sleeve includes access ports for both the thru lumen 144 and the inflation lumen 146. The thru lumen spans the entire length of the balloon catheter and exits at tip 148 at the distal end of balloon 116. The inflation lumen 146 is coupled to balloon 116 so that the balloon can be inflated by delivery of a liquid, such as water, a gas, such as air, or the like.

In some embodiments, for delivery of apparatus 100, support 110 is tightly furled about deflated balloon 116 and placed with within a sheath (not shown). During deployment, this sheath is retracted along the shaft to expose support 110. In alternative embodiments, an elastic member (not shown) may be coupled to the support 110 to keep the support furled around balloon 116 during deployment of apparatus 100

Apparatus 100, illustrated in FIG. 4, is designed for use with the RF energy methods as set forth herein. Electrode array 112 can be activated with approximately 300 watts of radio frequency power for the length of time necessary to deliver from 1 J/cm$^2$ to 50 J/cm$^2$ To determine the appropriate level of energy, the diameter of the lumen is evaluated so that the total treatment area can be calculated. A typical treatment area will require total energy ranging from 1 J/cm$^2$ to 50 J/cm$^2$.

In order to effectively ablate the mucosal lining of the esophagus and allow re-growth of a normal mucosal lining without creating damage to underlying tissue structures, it is preferable to deliver the radiofrequency energy over a short time span in order to reduce the effects of thermal conduction of energy to deeper tissue layers, thereby creating a "searing" effect. It is preferable to deliver the radiofrequency energy within a time span of less than 5 seconds. An optimal time for effective treatment is less than 1 second, and preferably less than 0.5 second or 0.25 seconds. The lower bound on time may be limited by the ability of the RF power source to deliver high powers. Since the electrode area and consequently the tissue treatment area can be as much as several square centimeters, RF powers of several hundred watts would be required in order to deliver the desired energy density in short periods of time. This may pose a practical limitation on the lower limit of time. However, an RF power source configured to deliver a very short, high power, pulse of energy could be utilized. Using techniques similar to those used for flash lamp sources, or other types of capacitor discharge sources, a very high power, short pulse of RF energy can be created. This would allow treatment times of a few milliseconds or less. While this type of approach is feasible, in practice a more conventional RF source with a power capability of several hundred watts may be preferred.

For an apparatus 100 employing a different length electrode array 112, or balloon 116 is expanded to a different diameter, the desired power and energy settings can be scaled as needed to deliver the same power and energy per unit area. These changes can be made either automatically or from user input to the RF power source. If different treatment depths are desired, the geometry of electrode array 112 can be modified to create either a deeper or more superficial treatment region. Making the electrodes of array 112 more narrow and spacing the electrodes closer together reduces the treatment depth. Making the electrodes of array 112 wider, and spacing the electrodes further apart, increases the depth of the treatment region. Non-uniform widths and spacings may be exploited to achieve various treatment effects.

In order to ensure good contact between the esophageal wall and electrode array 112, slight suction may be applied to the through lumen tube to reduce the air pressure in the esophagus 14 distal to balloon 116. The application of this slight suction can be simultaneously applied to the portion of the esophagus 14 proximal to balloon 116. This suction causes the portion of the esophageal wall distended by balloon 116 to be pulled against electrode arrays 112 located on balloon 116.

Various modifications to the above mentioned treatment parameters with electrode array 112 can be made to optimize the treatment of the abnormal tissue. To obtain shallower lesions, the radiofrequency energy applied may be increased while decreasing the treatment time. The patterns of electrode array 112 may be modified, such as shown in FIG. 7, to improve the evenness and shallowness of the resulting lesions. The devices and methods of the present invention can also be modified to incorporate temperature feedback, resistance feedback and/or multiplexing electrode channels.

Because the size of the lumen to be treated will vary from patient to patient, the device of the present invention is configured to variably expand to different diameters while maintaining a uniform and constant density of electrodes in contact with the tissue surface. In one embodiment of the present invention shown in FIGS. 10 and 11, an electrode array is arranged on a support 160 comprising a flexible electrode backing that is axially furled inside a cylindrical container 162. Support 160 may comprise a non-distensible, rectangular-shaped thin sheet formed from a polymer material, such as polyimide. An expandable member 164, such as an elastic balloon, surrounds a portion of the outside surface of container 162, leaving access to an opening that is formed from an axial slot 166 down the center of container 162. One end of support 160 is partially unfurled through slot 166 of container 162, and around the circumference of the expandable member 164 until it again reaches slot 166 where it is attached to either expandable member 164 or container 162

Figure 11:
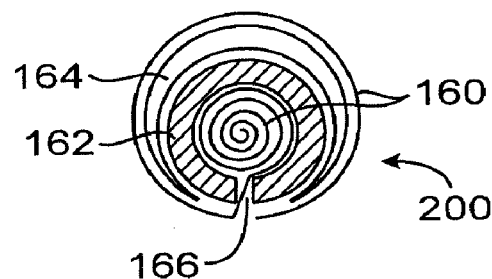
FIG. 11 is an enlarged cross-sectional view of the device of FIG. 10 in a compressed configuration.

FIG. 11 illustrates the apparatus 200 of the present invention in its compressed configuration. To engage the inner surface of a lumen that is larger than the compressed diameter of the catheter, expandable member 164 is incrementally deployed until the desired pressure is exerted on the inside wall of the lumen. In the method of this invention, it is desirable to deploy the expandable member 164 sufficiently to occlude the vasculature of the submucosa, including the arterial, capillary or venular vessels. The pressure to be exerted to do so should therefore be greater than the pressure exerted by such vessels, typically from 1 psig to 20 psig, usually from 5 psig to 10 psig. When the expandable member 164 is inflated, support 160 unfurls from the container 162, exposing additional electrodes to compensate for the increased surface area. Although the surface area of the electrode array increases, electrode density on the surface of support 160 remains constant. Energy, including but not limited to an RF signal, may then be delivered to the electrodes to facilitate a uniform treatment to a precise depth of tissue. After the treatment has been administered, the expandable member 164 is collapsed so that the apparatus 200 may be removed from the lumen, or reapplied elsewhere.

Suitable expandable members 164 include but are not limited to a balloon, balloon with a tapered geometry, basket, plurality of struts, an expandable member with a furled and an unfurled state, one or more springs, foam, bladder, backing material that expands to an enlarged configuration when unrestrained, and the like. A balloon-type expansion member 164 may be elastic, or a non-distensible bladder having a shape and a size in its fully expanded form, which will extend in an appropriate way to the tissue to be contacted. In one embodiment shown in FIG. 12, container 162 may be centered within expansion member 164, such that expansion member 164 forms a "c" shape around container 162

In another embodiment, electrode support 160 can be formed from an electrically insulating polymer, with an electroconductive material, such as copper, deposited onto a surface. An electrode pattern can then be etched into the material, and then the support can be attached to or furled around an outer surface of a balloon. Bay way of example and without limitation, the electrode pattern may be aligned in an axial or traverse direction across the support, formed in a linear or non-linear parallel matrix or series of bipolar pairs, or other suitable pattern as illustrated in FIGS. 5, 6 and 7.

Figure 12:
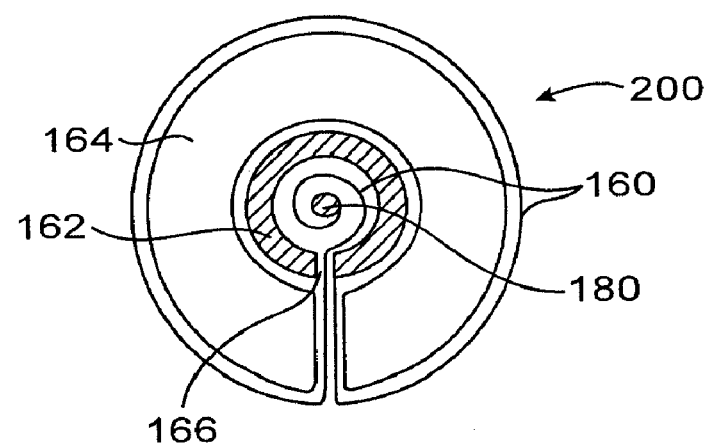
FIG. 12 shows an enlarged cross-sectional view of another embodiment of a device of the invention in an expanded configuration

In yet another embodiment illustrated in FIG. 12, electrode support 160 is attached to a shaft 180, upon which support 160 is spirally coiled inside container 162. Shaft 180 rotates freely as the support is uncoiled from the expansion of balloon 164. After treatment has been administered, shaft 180 can be rotated in the opposite direction to recoil support 160 into the container, thereby facilitating removal of apparatus 162 from the lumen. Shaft 180 may also be coupled with a torsion spring (not shown) so that a retraction and/or constant torsional force is applied to the support 160 to keep the support snug against balloon 164 as it expands or compresses.

Figure 13:
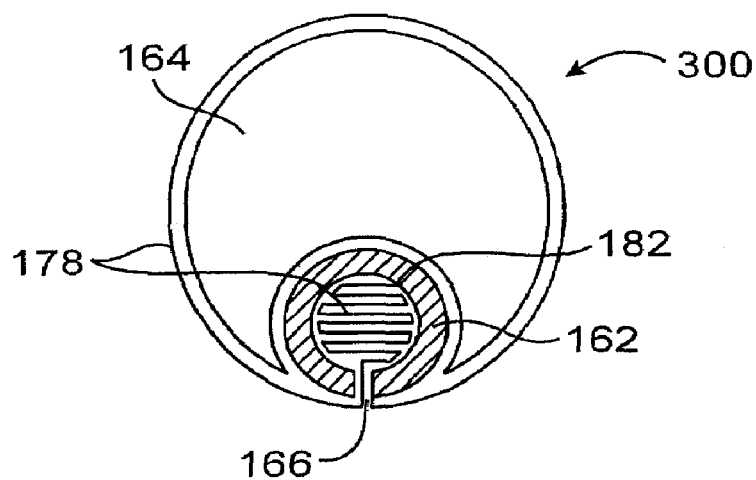
FIG. 13 shows an enlarged cross-sectional view of yet another embodiment of a device of the invention in an expanded configuration.

FIG. 13 illustrates another embodiment of the present invention utilizing a pleated electrode support. The electrode support 178 of apparatus 300 is repeatedly folded upon itself in an accordion-like pattern and attached at a first end 182 to the inside wall of container 162. The support 178 passes through slot 166 of the container and around balloon 164 to the inside wall of slot 166 where it is attached at its second end. When balloon 164 is expanded, the pleats of support 178 unfold, deploying the previously shielded electrodes to accommodate the increase in surface area of the balloon.

Figure 14A:
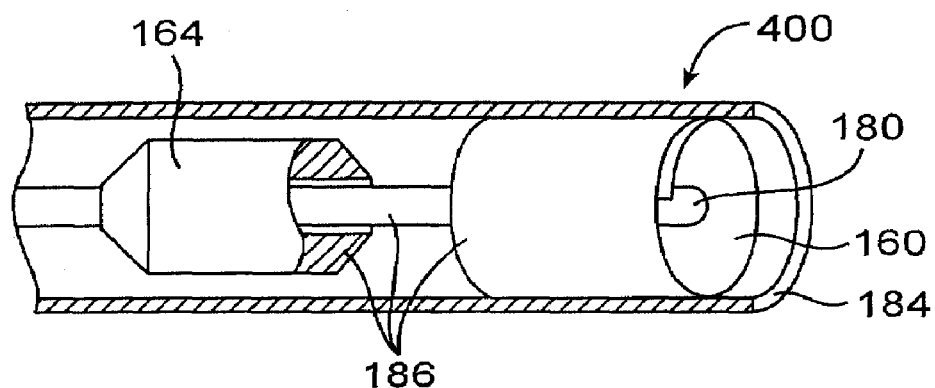
FIG. 14A is a perspective cross-sectional view of another embodiment of a device of the invention in a compressed configuration.
Figure 14B:
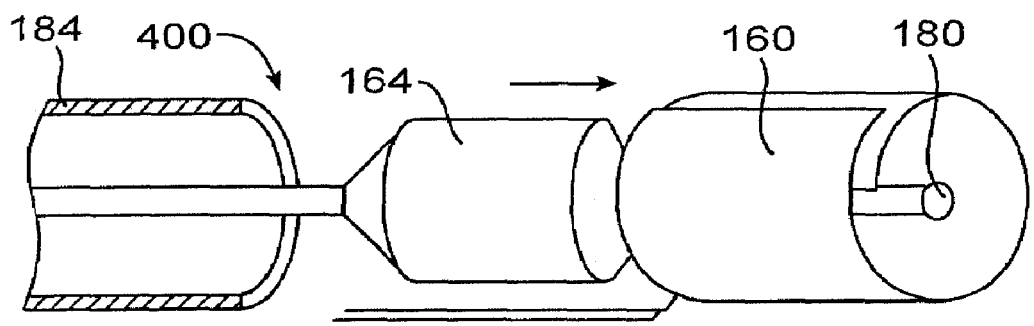
FIG. 14B is a perspective cross-sectional view of the device of FIG. 10 in a compressed configuration.

FIGS. 14A and 14B show an electrode deployment device 400 wherein electrode support 160 is attached to and spirally furled about the distal end of shaft 180. An expandable balloon 164 is positioned on shaft 180 proximal to support 160, and is mounted on shaft 180 so that it can freely slide axially along the shaft. Support 160 is retained in a compressed state by sheath 184, which shields both the support and balloon 164 from the interior walls of the lumen while the device 400 is advanced to the treatment region. When the device 400 is at the appropriate location, the catheter assembly 186 is advanced out of the sheath 184, causing the electrode support 160 to slightly expand. The balloon 164 is then advanced to the distal end of the shaft 180 so that it is surrounded by the inside circumference of the support 160. Balloon 164 is then expanded to match the inside diameter of the treatment region, further exposing additional electrodes on the support as it unfurls to accommodate the increase in surface area of the balloon.

Figure 15A:
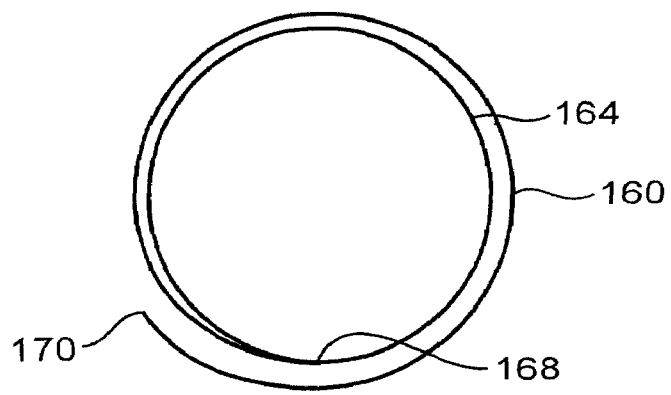
FIG. 15 shows enlarged cross-sectional views of several embodiments of a device of the invention in an expanded configuration.
Figure 15B:
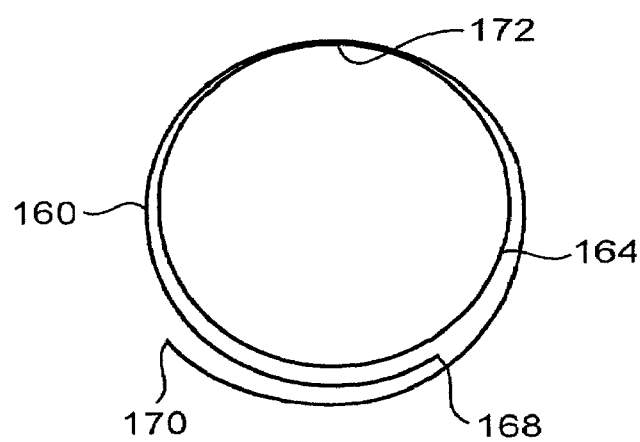
Figure 15C:
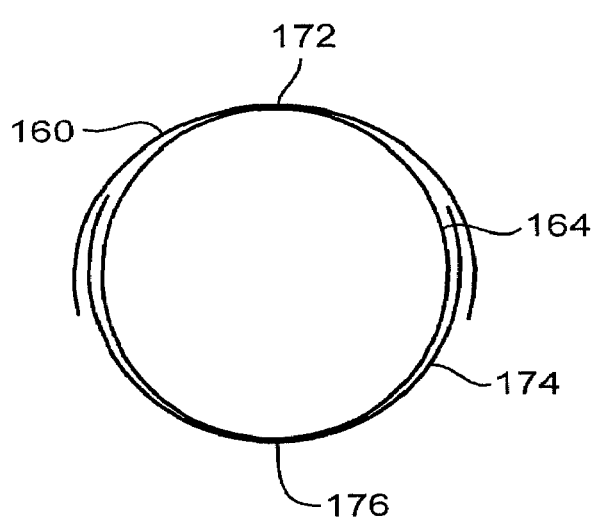

FIGS. 15A-C illustrate additional embodiments of the electrode support 160 of the present invention. In FIG. 15A, support 160 is attached at a first end 168 to a expandable balloon 164. The second end 170 of the support 160 is furled around the balloon, overlapping the first end 168. In FIG. 15B, support 160 is attached at its midpoint 172 to expandable balloon 164, the ends of the support furling around the balloon in opposite directions such that the first end 168 is overlapped by the second end 170. As the balloon 164 expands, the support 160 unfurls and further exposes additional electrodes that had previously been shielded by the overlapping portion of the support FIG. 15C illustrates another embodiment of the present invention utilizing two separate electrode array supports. A first support 160 is attached at its midpoint 172 to an expandable balloon 164, the ends of the first support furling around the balloon in opposite directions. A second support 174 is also attached at its midpoint 176 to the balloon 164 opposite from the first support 160, the ends of the second support 174 also being furled in opposite directions around the balloon and overlapping the ends of the first support 160. One or more elastic members (not shown) are attached to the ends of the second support and another point on the first support. As the balloon is expanded, the elastic members allow the supports to unfurl with respect to each other and further expose additional electrodes of the first support that had previously been shielded by the overlapping portion of the second support.

Figure 8:
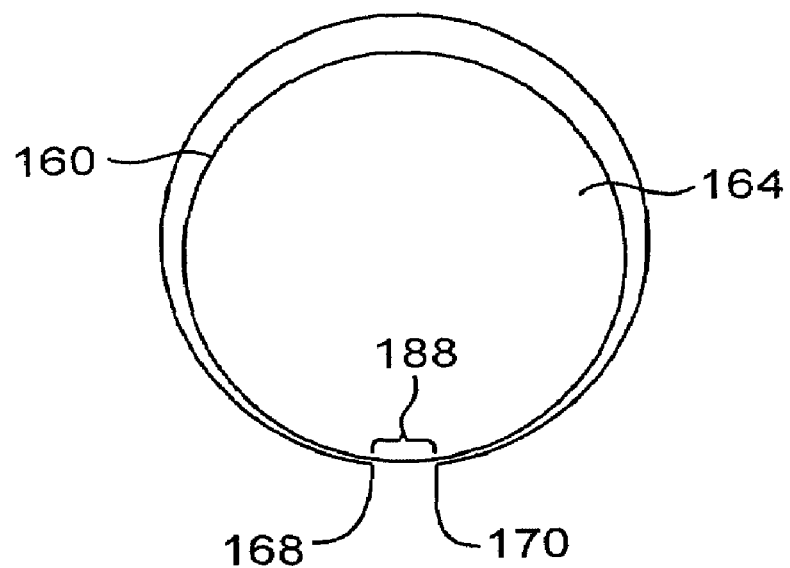
FIG. 8 is an enlarged cross-sectional view of a device of the invention in an expanded configuration.
Figure 9:
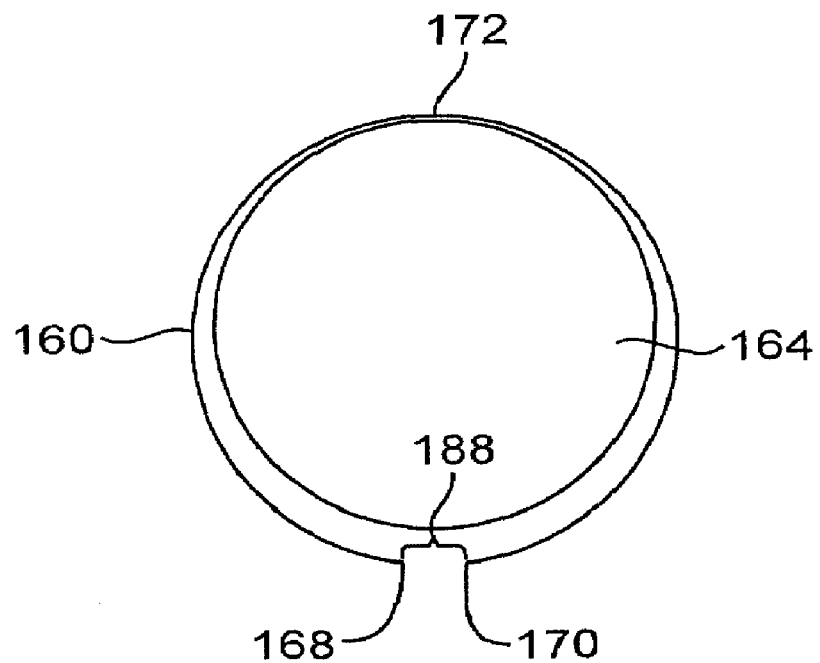
FIG. 9 shows an enlarged cross-sectional view of the device of FIG. 8 in a more expanded configuration.

FIG. 8 illustrates another embodiment where the support 160 is furled around balloon 164 in a non-overlapping configuration. In the depicted embodiment, support 160 is attached at one end 168 to the balloon 164 and the second end 170 is furled around the circumference of the balloon until it reaches the first attached end, where it terminates. When balloon 164 expands, the ends of the support expand with it, forming a gap 188 between each end that increases with the increasing circumference of the balloon. One advantage of this configuration is that the electrode surface area remains constant when the balloon is expanding. However, a portion of the circumference will be void of a treatment surface due to the gap in the electrode support. In alternative embodiments shown in FIG. 9, the non-overlapping support 160 may also comprise one or more supports that are attached at their midpoint 172, such that ends 168 and 170 form gap 188 when the balloon 164 is expanded.

Figure 17:
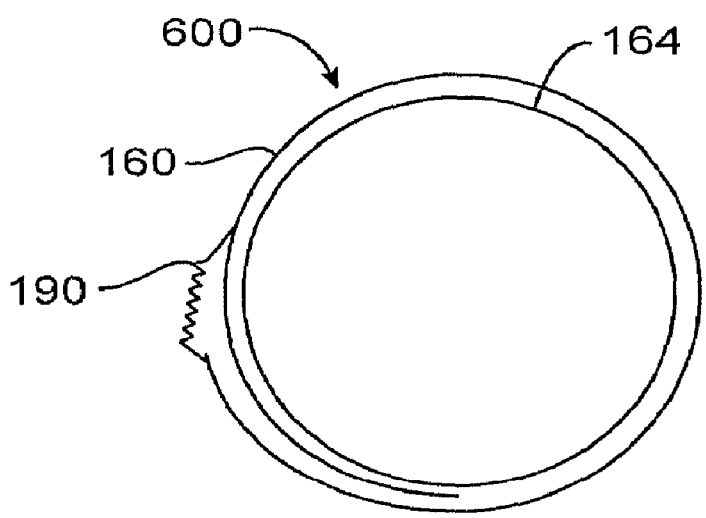
FIG. 17 shows an enlarged cross-sectional view of another embodiment of a device of the invention in an expanded configuration.

In various embodiments, one or more elastic members are attached to the support to prevent the support from prematurely unfurling. As illustrated in FIG. 17, elastic member 190 is attached to one end of electrode support 160 and to another point on the support free of electrodes. The elastic member 190 keeps the furled support 160 at a basic diameter smaller than that of the lumen to be treated. An expandable balloon 164 is then inserted within the inner diameter of support 160, and the assembly 600 is advanced to the treatment site where balloon 164 is expanded to engage the inner surface of the lumen. As balloon 164 is expanded, the elastic member 190 allows the support to unfurl and further expose additional electrodes while also keeping the free end of support 160 from shifting out of alignment with the remainder of the array. After treatment has been administered, elastic member 190 recompresses support 160 while balloon 164 deflates, returning support 160 to a reduced diameter to facilitate removal of the assembly 600 from the lumen.

Figure 16:
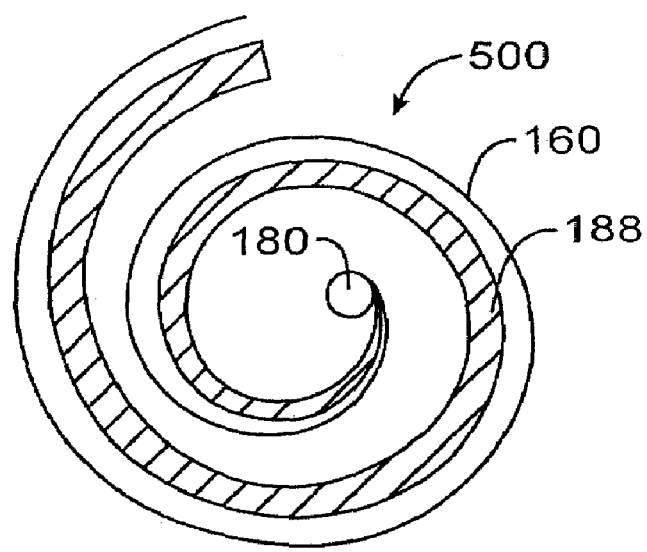
FIG. 16 is an enlarged cross-sectional view of another embodiment of a device of the invention in an expanded configuration.

FIG. 16 shows an electrode deployment device 500 wherein electrode support 160 is attached to a spiral spring 188. Spring 188 may include, but is not limited to a wire, series of wires, or strip or sheet of a spring temper or superelastic material that provides a retraction and/or a constant stress or force while compressed, such as a 316 stainless steel or nitinol. It should be noted however, that any material suitable as a retraction and/or a constant force spring may be used. Spring 188 is attached at one end to a shaft 180. To facilitate treatment, the spring 188 and support are coiled about shaft 180 and placed inside a sheath (not shown). Device 500 is then advanced to the treatment region, and the sheath is retracted, causing the spring 188 to expand and mate with the wall of the lumen.

Figure 18:
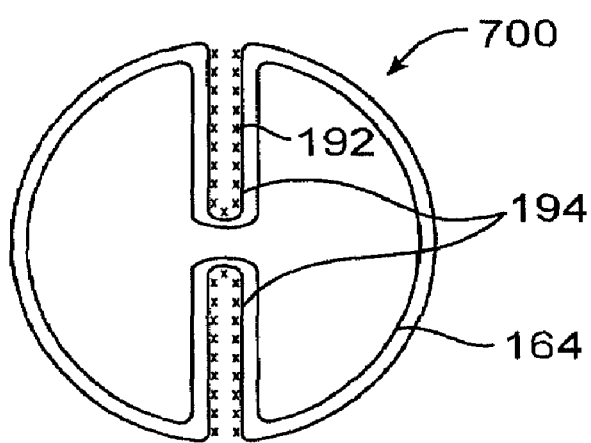
FIG. 18 is an enlarged cross-sectional view of yet another embodiment of a device of the invention in a partially expanded configuration.

FIG. 18 illustrates another embodiment of the present invention utilizing an adhesive to compress a pre-selected electrode array. Apparatus 700 includes a flexible electrode support 160 that is folded into a loop and attached at its ends. The edges of a portion of support 160 are coated with an adhesive 192 in a region where the adhesive will not cover the conductive elements of the electrode. The support 160 is creased upon itself at the adhesive regions to form one or more folds 194 of unexposed electrodes. The adhesive 192 that is applied will preferably not form a strong bond, but rather have a low adhesive quality so that a reasonable amount of deployment force will allow the bond to pull apart and deploy and expose only the amount of electrode area required to have complete circumferential contact with the lumen. An expansion balloon 164 is positioned within the looped support 160. The apparatus 700 is then advanced to a treatment region, and the balloon 164 is inflated. As balloon 164 expands, the pressure on the support increases, forcing the folds 194 to separate and incrementally expose additional electrodes on the support. The diameter of the apparatus 700 increases until the proper engagement with the lumen wall is achieved.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A method for treating tissue in an esophagus, the method comprising:
   inserting an electrode deployment apparatus into an esophagus, the electrode deployment apparatus comprising an array of electrodes arranged on an exterior surface of an expandable support in a pre-selected electrode density at a first expansion size;
   radially expanding the expandable support to a second expansion size to engage electrodes with a wall of the esophagus while maintaining the electrode density of the engaged electrodes about the exterior surface of the support; and
   delivering energy from the electrodes to the esophagus.

2. The method of claim 1, wherein the expandable support is dimensionally stable.

3. The method of claim 1, wherein the electrode deployment apparatus further comprises an expansion member coupled to the expandable support.

4. The method of claim 3, wherein the expandable support is furled about an axis and wherein expanding the support radially comprises unfurling the support to selectively expose a portion of the array.

5. The method of claim 4, wherein unfurling comprises expanding the expansion member.

6. The method of claim 5, wherein expanding the expansion member comprises inflating a balloon.

7. The method of claim 6, wherein expanding the expansion member comprises unfurling the support by applying force against a retaining elastic member adapted to retain the support from unfurling freely.

8. The method of claim 7, further comprising removing the force against the elastic member after delivering energy to the esophagus.

9. The method of claim 3, wherein the electrode deployment apparatus further comprises a movable shield associated with the expansion member, the expanding step comprising exposing at least a first portion of the array and shielding a second portion of the array.

10. The method of claim 1, wherein the energy is radiofrequency energy applied through a multiplicity of bipolar electrode pairs in the array.

11. The method of claim 10, wherein the electrodes are parallel, have a width in the range from 0.1 mm to 3 mm, and are spaced-apart by a distance in the range from 0.1 mm to 3 mm.

12. The method of claim 11, wherein the radiofrequency energy is delivered at a total dosage in the range from 1 joules/cm$^2$ to 50 joules/cm$^2$.

13. The method of claim 12, wherein the radiofrequency energy is delivered over a time period below 5 seconds.

* * * * *